United States Patent [19]

Aivasidis et al.

[11] Patent Number: 5,096,814
[45] Date of Patent: Mar. 17, 1992

[54] MACROPOROUS AND MICROPOROUS INORGANIC CARRIER FOR IMMOBILIZATION OF CELLS

[75] Inventors: Alexander Aivasidis, Juelich; Christian Wandrey, Juelich-Stetternich; Werner Kiefer, Mainz-Finthen, all of Fed. Rep. of Germany

[73] Assignees: Kernforschungsanlage Juelich GmbH, Juelich; Schott Glaswerke, Mainz, both of Fed. Rep. of Germany

[21] Appl. No.: 456,422

[22] Filed: Dec. 29, 1989

Related U.S. Application Data

[63] Continuation of Ser. No. 149,989, Jan. 28, 1988, abandoned, which is a continuation of Ser. No. 715,314, Mar. 25, 1985, abandoned, which is a continuation-in-part of Ser. No. 579,539, Feb. 13, 1984, Pat. No. 4,588,540.

[30] Foreign Application Priority Data

Mar. 23, 1984 [DE] Fed. Rep. of Germany ....... 3410650

[51] Int. Cl.$^5$ .............. C12P 1/00; C02N 11/14; C02N 5/00; C02F 3/00
[52] U.S. Cl. .................... 435/41; 210/601; 210/606; 264/43; 435/176; 435/240.23; 435/240.24; 435/288
[58] Field of Search ........... 435/41, 176, 288, 240.23, 435/240.24; 264/43; 210/601, 606; 65/18.1; 502/7, 407

[56] References Cited

U.S. PATENT DOCUMENTS

| | | | |
|---|---|---|---|
| 3,992,329 | 11/1976 | Eaton et al. | 435/176 X |
| 4,153,510 | 5/1979 | Messing et al. | 435/176 |
| 4,321,141 | 3/1982 | Messing | 435/176 X |
| 4,588,540 | 5/1986 | Kiefer et al. | 65/18.1 |

OTHER PUBLICATIONS

Durand et al., Process Biochemistry, Sep., 1978, pp. 14–23.
Huysman et al., "Factors Affecting the Colonization of Non Porous and Porous Packing Materials in Model Upflow Methane Reactors", Biotechnology Letters, vol. 5, No. 9, pp. 643–648 (1983).

*Primary Examiner*—David M. Naff
*Attorney, Agent, or Firm*—Millen, White & Zelano

[57] ABSTRACT

For the immobilization of micro-organisms and animal cells, in particular for anaerobic processes, such as the purification of waste water or for the biotechnological production of nutrition-essential or pharmacological substances, porous, sintered bodies are employed (inorganic carrier bodies). In particular, sintered glass in the form of Raschig rings with a double-pore structure, are employed. They have porosity-determining throughgoing macropores that permit a free exchange of fluid and gas from the interior of the carrier to the surroundings, and open micropores within the macropore walls, the diameter of the micropores being of the same order of magnitude as the size of the micro-organisms or cells. These carrier bodies typically have an open pore volume of 35% to 85%, 20% to 80% being accounted for by the macropores having a diameter of 20 to 500 μm, and 5%–50% by micropores having a diameter of 1–10 μm. These bodies are obtained by sintering a powder mixture comprising fine-grain material and a coarse-grain substance melting at a higher-than-sintering temperature and separable from the sintered product by allowing the latter to cool and separating (dissolving) out the soluble component.

33 Claims, 6 Drawing Sheets

1000μm

100μm

10μm

100μm

10μm

MACROPOROUS AND MICROPOROUS INORGANIC CARRIER FOR IMMOBILIZATION OF CELLS

This is a continuation of Ser. No. 07/149,989, filed Jan. 28, 1988, abandoned which is a continuation of Ser. No. 06/715,314, filed Mar. 25, 1985, abandoned which is a continuation in-part of Ser. No. 06/579,539, filed Feb. 13, 1984, now U.S. Pat. No. 4,588,540, issued May 13, 1986.

BACKGROUND OF THE INVENTION

This invention relates to a procedure for the immobilization of micro-organisms and animal cells, in particular for anaerobic processes on porous, inorganic carrier bodies, to the subsequently obtained carrier bodies bearing a growth of micro-organisms, and to the carrier bodies suitable for immobilization, inter alia.

The immobilization of micro-organisms and cell material on solid bodies provides a means of providing such materials in abundance at a desired site. This is of significance in particular in the case of biotechnological processes. Both aerobic and anaerobic biotechnological processes should produce as high a space-time yield (substrate "turnover" per volume and time unit) as possible. This requirement can be met all the more readily, the greater the concentration of the active cells serving a production and catalyst role simultaneously.

High concentrations of cells are readily achieved in aerobic systems, where cell growth occurs virtually unhindered. In anaerobic systems, in contrast, cell growth is subjected to a limitation from the beginning, so that only relatively low biomass concentrations are achieved. In recent times, however, it is just these anaerobic systems that have attracted particular attention due to the favorable energy balance involved (e.g., biogas formation on the one hand, and no need for energy expenditure for the oxygen supply necessary for aerobic systems on the other). It has bene recognized that, using such systems and with little energy, it is often possible to produce valuable disproportionated products from inexpensive substrates. A particular example of this is the anaerobic treatment of highly concentrated waste water, resulting in the conversion of up to 95% of the organic contamination into biogas, with the simultaneous production of only 3–4% biomass. The low growth of micro-organisms in anaerobic systems makes it especially necessary to "hold back" and concentrate the biomass. This may also be of interest in the case of aerobic systems, for example, in the solution of separating problems.

For this reason, the immobilization of micro-organisms on solid carriers has long been practiced and investigated. In this connection, inexpensive, readily available carrier materials from the environment, such as sand, lava rocks, ceramics, activated charcoal, anthracite, glass, etc., have been investigated. With these, a more or less good immobilization of the micro-organisms can be accomplished More recently, more organic carrier materials have attracted interest: Thus, I. Karube et al (Biotechnol. Bioeng. Vol. 22 (1980), pages 847–857), describes a study of the immobilization of methane-producing bacteria on polyacrylamide gel, agar gel and collagen membranes, of which only the agar gel was found to be suitable. At the same time, however, attention was drawn to the low diffusion capacity of the nutrients and of methane through the agar gel. P. Scheter et al (Biotechnol. Bioeng Vol 30 23 (1981), pages 1057–1067) reported the immobilization of Methanosarcina barkeri on a $Ca^{2+}$- cross-linked alginate network, which was studied in the form of pellets with diameters varying between 1.2 and 3.7 mm. In this report, in contrast to that of P.S.J. Cheetham et al (Biotechnol. Bioeng. Vol. 21 (1979) 2155 ff.) who maintained that substrate transport into the alginate pellets is delayed, no difference in the activity of the micro-organisms dependent on the diameter of the pellets was found.

On the occasion of the 5th Symp. Techn. Mikrobiol. held in Sept. 82 in Berlin, B. Kressdorf et al reported on the immobilization of yeasts and bacteria by Ca-alginate gel. Comparative investigations with a variety of different types of carriers were described; cross-linked alginate microspheres of high solidity and a diameter of less than 1 mm bearing biomass, were said to be particularly useful.

Comparative investigations were also carried out by P. Huysman et al (Biotechn. Letters, Vol. 5 Nr. 9, (1983), pages 643–648). The carrier materials they studied were particles—about 5 mm in size—of sepiolite, zeolite, Argex (fire-expanded clay with surface pores of 0.1–7.5 $\mu$m), and glass beads, all examples of "non-porous materials", and, as examples of "porous materials", natural sponge with a porosity of about 50% and pore sizes varying from the $\mu$m range to the cm range, and non-cross-linked polyurethane foam with a porosity of about 30% and pore sizes varying from the $\mu$m to the mm range, and, finally, various sorts of cross-linked polyurethane foams with a porosity of 97% and uniform pore diameters of (a) 2.21 mm; (b) 430 $\mu$m and (c) 270 $\mu$m. Finally, polyurethane foam, coated with bentonite, with a uniform pore size of 430 $\mu$m was also incorporated into the study. It was established that of the "non-porous materials", only sepiolite revealing on crystalographic examination fine bundles of needle-like crystals having a length of 2 $\mu$m, permitted a useful formation of colonies. The bundles of "needles" revealed numerous gaps of a size corresponding to that of bacteria. The porous materials however, proved to be particularly suitable, the leading factor being found to be the great porosity and the size of the pores. In particular, the material having 430 $\mu$m pores and a porosity of 97%, with and without a coating of bentonite, produced favorable results. With this cross-linked polyurethane foam material, within a period of 2 weeks, approximately 25 liters of biogas (65% methane) per liter of reactor a day were produced.

In DE-OS 28 39 580, a number of porous carrier materials, in particular glass frits, are indicated for the immobilization of micro-organisms, 70% or more of the pores of which are at least as large as the smallest dimension of the micro-organisms, but smaller than 4 to 5 times the greatest dimension (in yeast cells or bacteria). It was established that both non-porous boron silicate glass, and also glass frits with pores larger than 20 $\mu$m in diameter, were appreciably poorer than material bearing pores of less than 20 $\mu$m.

Despite the numerous different investigations into carrier materials, and the development of, in part very useful, carrier bodies, however, the problem of immobilization of micro-organisms has not yet been resolved completely satisfactorily. In individual situations, different aspects, such as density, abrasion resistance, stability, long-term behavior, wettability and the like, are problematical. Consequently, the general objective of a particularly high level of effectiveness of the immobilized biomass has not yet been achieved.

SUMMARY OF THE INVENTION

Thus, it is an object of this invention to provide a way to immobilize micro-organisms and cell materials, so that a high concentration of biomass, coupled with a high level of bioactivity can be accomplished.

It is another object to ameliorate or eliminate the foregoing problems and provide the mentioned advantages.

Upon further study of the specification and appended claims, further objects and advantages of this invention will become apparent to those skilled in the art.

These objects have been achieved by providing an immobilization procedure of the type mentioned above, wherein, as carrier body, there are used porous sintered bodies having a double-pore structure with porosity-determining, through-going macropores permitting the free exchange of liquid and gas from the inside of the body to the external surroundings, and, within the macropore walls, open micropores with a diameter of the order of the size of the micro-organisms or cells.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein: the following figures show electron-microscopic enlargements of a glass structure revealing the advantageous structure of the material, e.g.

DETAILED DISCUSSION OF THE INVENTION

Figure 1A:
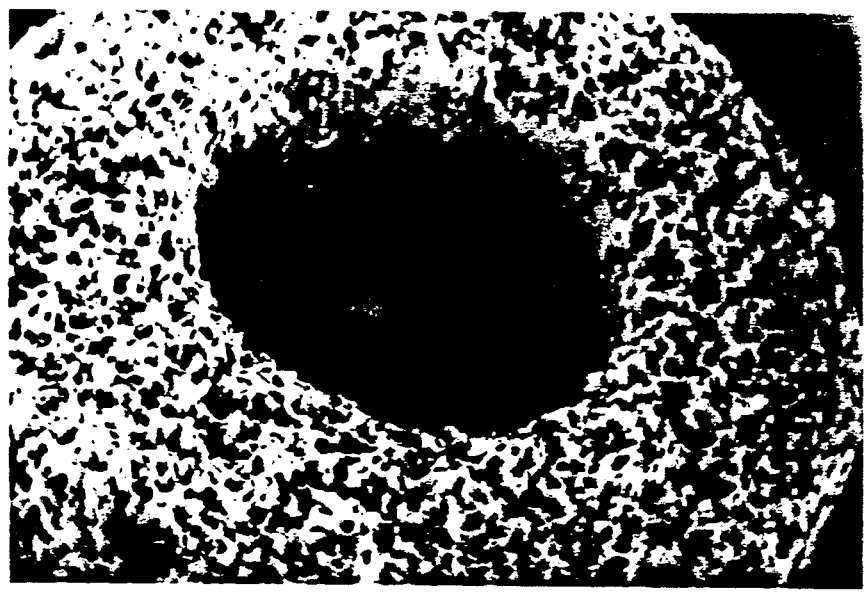
FIG. 1a shows the surface of a Raschig ring sintered glass body (enlargement × 19)
Figure 1B:
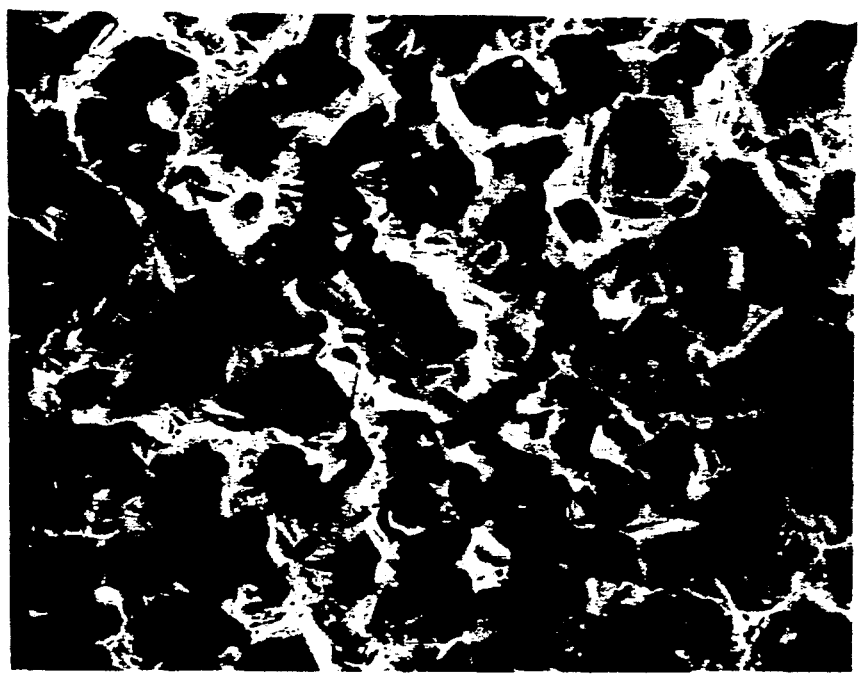
FIG. 1b shows the cut surface of such a body with a porosity of 60%, and a size of the macropores of 60 to 100 μm (enlargement × 104)
Figure 1C:
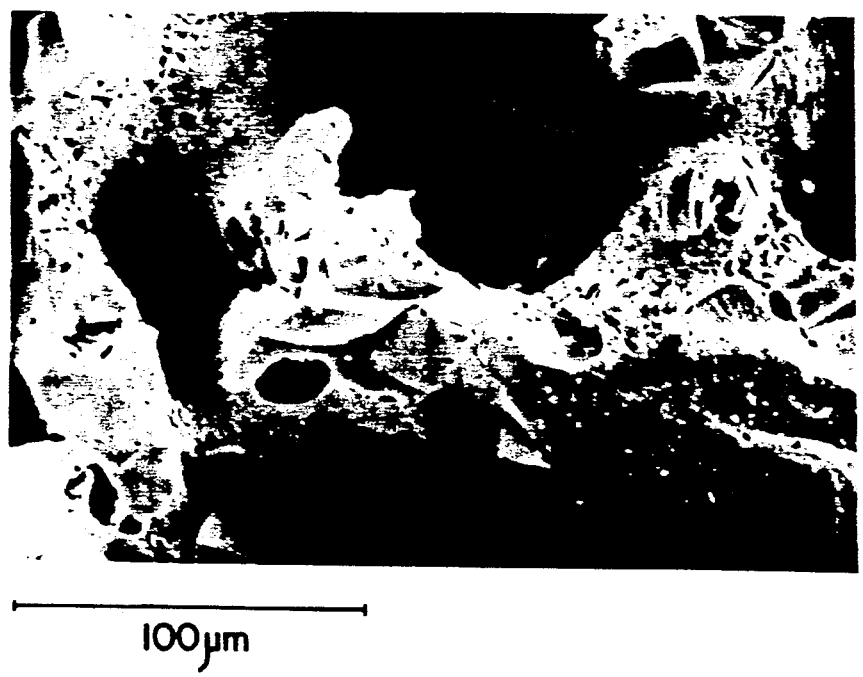
FIG. 1c shows the cut surface of such a body enlarged 512 times.
Figure 1D:
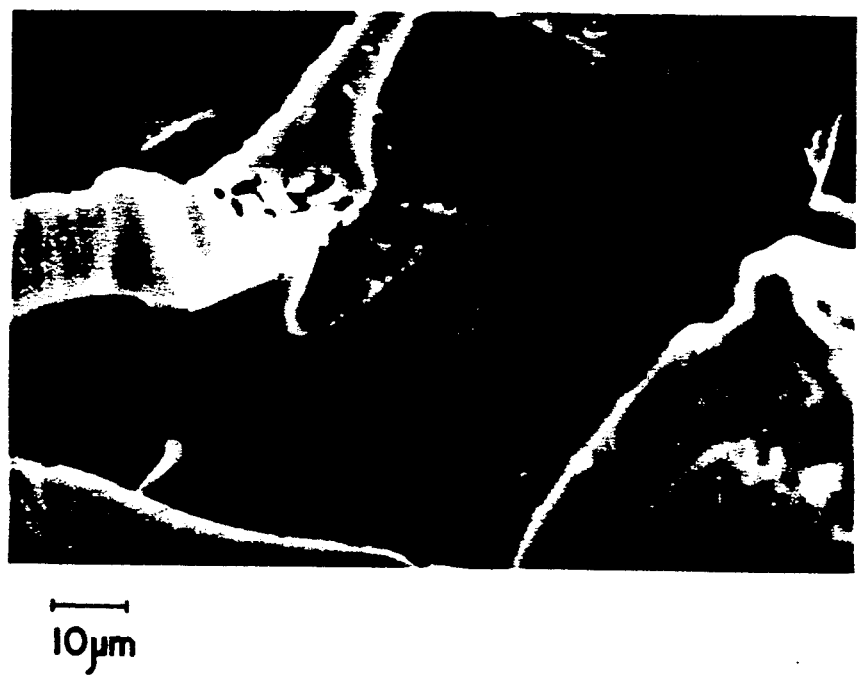
FIG. 1d shows the cut surface of such a body enlarged 1040 times.
Figure 2A:
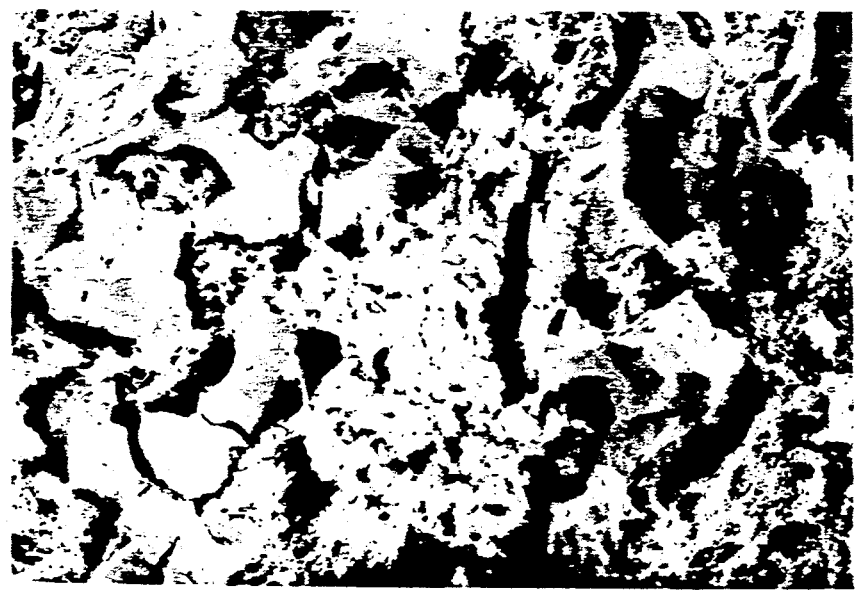
FIGS. 2a and 2b show sintered glass bodies bearing a growth of micro-organisms after four months reactor operation (enlargement × 200 and × 5040, respectively).
Figure 2B:
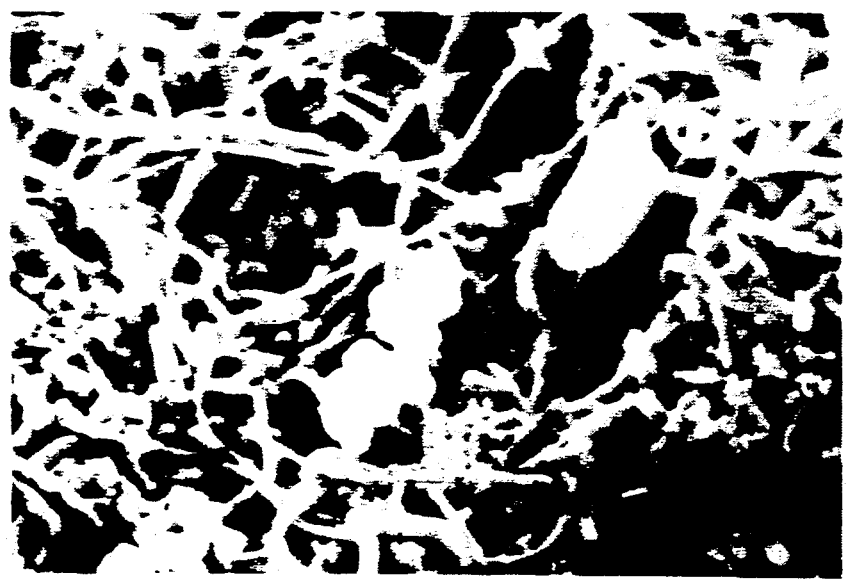

Surprisingly, it has been shown that the use of porous sintered bodies of the above-mentioned type, leads to a considerable increase in the effectiveness of bioprocesses. A decisive factor in this connection is the special structure of the carrier material. On account of its through-going macropores, the interior is freely accessible to the surrounding fluid, so that the "inflow" of material to be degraded, and the "outflow" of metabolic products, are not hindered. Thus, by "through-going" is meant such an accessibility property of the interior, wherein the body can be permeated throughout by a liquid upon its entry from essentially any macropore, because the macropores are connected to one another and the macropores on the surface are open.

The fine-pore "fissured" configuration of the pore walls of the sintered material is the portion which primarily favors the immobilization of the biomass or micro-organisms. An aim of this invention is to achieve as high a porosity of the material as possible, coupled with adequate mechanical stability. For this reason, carriers with a porosity of more than about 85% are less preferred. Similarly porosities of less than about 35% are also of little interest. Preferred are porosities in excess of 40%, in particular of 50% to 70% or, more preferably, 55% to 65%. Here, porosity refers to the % of the body's total volume occupied by pores. It is measured fully conventionally by microscopy and electron microscopy.

The diameter of the macropores can be routinely selected to suit the conditions of the individual application, and will usually not exceed about 500 μm. Macropores in the range of 20 to 250 μm, and in particular the range 50 to 150 μm, have proved particularly expedient. In general, a suitable diameter of the micropores is about 1 to 10 μm. The contribution of the micropores to the overall pore volume usually lies between 5 and 15%, depending upon the size ratio of the micropores to macropores, and the overall porosity; for mechanical reasons high porosities generally permit only a low percentage of micropores. Micropores are feasible and compatible with the end-use in mind, e.g., are of a size on the order of the size of the micro-organisms.

In particularly preferred aspects, a carrier body is employed, which has an open pore volume of 35% to 85%, with 20% to 80% macropores having a diameter of 20 to 500 μm, and 15%–5% micropores having a diameter of 1–10 μm, or in which the entire open pore volume lies between 50% and 70%, preferentially between 55% and 65%, and the percentage of micropores <10 μm is 10% to 5%.

The material of the carrier bodies does not need to be uniform, provided it is adequately sinterable and upon sintering forms the necessary porous microstructure. Preferred are glass, ceramics or glass-ceramics, in particular silicated material.

Essentially any glass, ceramic or glass-ceramic composition can be used in conjunction with this invention, as long as it is compatible with the end use micro-organisms or cells when in sintered form, e.g., soda-lime glass, boro-silicate glass, alumino-silicate glass, eucrystite-glass ceramics, cordiesite glass-ceramics or mixtures of 5 to 30% glass and 95 to 70% ceramic-materials.

A "silicated material" is a material which contains at least 40% by weight $SiO_2$.

The porous carrier material can be obtained by sintering a powder mixture comprising a fine-grain sinterable material, and a somewhat more coarse-grained substance melting at a higher-than-sintering temperature (e.g., a salt) and separable from the sintered material, e.g., by allowing the latter to cool and separating out the soluble components.

Typical separable materials are those in the general categories of inorganic salts. Examples of particularly preferred materials within these broad categories are alkali or alkaline earth-halogenides or -sulfates. In general, any material which can be dissolved in a solvent which does not also dissolve the sinterable material can be employed as long as the material and the solvent are compatible with the subsequent end-use, e.g., are not harmful in residue amounts to micro-organisms and/or animal cells. Typical such solvents which can be employed in conjunction with the separable materials include water and inorganic acids.

The pore volume and the mean diameter of the macropores are determined mainly by the amount of separable substance, and its grain size. The diameter of the micropores which, after separating (dissolving) out the soluble substance, perforate the walls of the (e.g., silicated) sintered structure, is determined primarily by the grain size of the sinterable material.

In particularly preferred aspects, the macropores have a size of 20 to 500 μm, and are obtained by the use of a soluble substance having a grain size of 20–500 μm, which is separable from the sintered product, or the micropores have a size of 1–10 μm and are obtainable by the use of a sinterable material having a grain size <40 μm, preferentially <20 μm.

The concept of sintering a sinterable material and a non-sinterable separable material as well as the sintering conditions are known from Patent application, U.S. Pat. No. 4,588,540 which is incorporated by reference herein.

To produce a carrier body which has an open pore volume of 35% to 85%, of 50% to 70% or of 55% to 65%, a content of the separable material in weight per cent is 20% to 80%, 40% to 65% and 45% to 60%, respectively.

To produce micropores of about 1 μm, glass powder of <20 μm is used, which has a grain size distribution of about 1 to 5 μm, and for micropores of about 10 μm glass powder of <40 μm is used with a grain size distribution of about 5 to 20 μm.

The typical size of the bodies overall in case of granules lies within the range of about 100 μm to the mm range. The size of cubes lies within the range of from about mm to about cm, and tubes, which can also be used in this invention, have diameters between some mm and some cm and lengths between mm's and m's.

An advantage of this procedure for the manufacture of carrier material for bioreactors is that both very fine and coarse pores are formed at one and the same time; while the micropores in the walls are too fine to allow the passage of liquid and, on account of their tiny size, are suitable for the immobilization of the micro-organisms, the macropores permit the rapid "inflow" of nutrients and the "outflow" of the metabolic products.

The glass frits per DE-OS 28 39 580 manufactured in accordance with the usual procedures, contain only fine or coarse pores. In the case of the glass frits and sinter materials employed, the pore diameter and pore volume are determined solely by the grain size of the sinter material. Thus, the walls of the large-pore sintered body are not "fissured" by fine pores.

Particularly favorable immobilization properties of the carrier enable high concentrations of highly active biomass to be achieved. These are possible, e.g., by the large interior surface and free accessibility of the colonies "anchored" in the hollow cavities which can grow within the carrier largely protected from abrasion, so that even poorly adhering populations can also be cultured. Also important is the selective "adjustability" of the structure via the manufacturing conditions which can be adapted to the micro-organisms to be immobilized and the nature and flow-conditions of the fluid in which it is to be applied. Furthermore, the porous sintered bodies are characterized by mechanical stability, good wettability and thermal stability, so that they are readily sterilizable. They are inexpensive and their composition is readily varied.

Thus, the porous sintered bodies can be made out of any compatible materials, in particular glasses, especially inexpensively out of waste glass. For the applications considered here, however, glasses containing biologically important trace elements, such as compounds of the elements nickel, molybdenum, copper, cobalt and the like are particularly useful. It is well-known that, despite its overall inert behavior, glass is subject to a certain exchange of ions with its surroundings, so that such trace elements contained within the material can have a promoting effect on the behavior of the microorganisms.

The immobilization of micro-organisms and animal cells according to the invention is, in view of the excellent properties of the corresponding porous sintered bodies bearing immobilized biomaterial, suitable for all biotechnological processes in which the bioactivity and simultaneous immobilization of such biomaterials are of use. At the present time, their use in anaerobic purification of waste water, in particular of special waste waters such as occur in the cellulose or paper industry or in cheese production, or the waste water produced by starch-manufacturing plants and breweries, are particularly expedient. In addition, micro-organisms immobilized in the manner of the invention are useful in the denitrification of water.

The biotechnological production of nutrition-essential and pharmacological substances is a further field of application of this invention as is the production of primary metabolites by fermentation processes. Such micro-organisms immobilized on porous sintered glass are useful for biotransformations to be performed on an industrial scale, such as the conversion of steroids and the like.

The excellent properties of the micro-organisms immobilized on a porous sintered body per this invention have been demonstrated on sintered glass in a fixed-bed reactor with vertical flow from bottom to top, with "overlayered" fluid circulation (by pH-controlled partial recycling). In the processing of evaporator condensate in the manufacture of cellulose, an increase in effectiveness (shortening of the average time requirement for comparable purification) by a factor of about 5 was achieved by replacing the previously used coarse-grain anthracite by porous sintered glass having a porosity of approximately 60% and a pore diameter of 60 to 120 μm, in the form of Raschig rings having a wall thickness of 2 mm and a height of 7 mm, all other conditions remaining identical.

The immobilization of the micro-organisms by porous sintered bodies with double-pore structure of this invention, so useful in particular for processes in fixed-bed reactors with an increased flow rate of the liquid through the fixed bed brought about by partial recycling, is, however, of course, also expedient for use in other types of reactors such as, for example, fixed-beds with horizontal through-flow. Depending upon the flow conditions involved, a certain adaptation of the macropores may be useful, the size of which should be increased as the relative velocity of the fluid with respect to the carrier decreases. The immobilization of micro-organisms on porous sintered bodies as effected in this invention, is also suitable for use in fluidized reactors, in which case, the sintered bodies are generally made smaller (e.g., <1 mm). When using a so-called "slurry reactor" (with a finely-divided catalyst suspension located between filter walls), more finely sub-divided material is used.

The large interior surface of the porous sintered body, with its freely accessible hollow cavities (provided with fine-pore "fissured" walls), which can be freely perfused by the fluid, so that the cells can be adequately supplied with nutrients, and the degradation products carried away, and whose finely configured wall structure offers the micro-organisms adequate opportunity for adhesion, makes possible the use of larger carrier body forms in fixed beds. This helps reduce the resistance to flow. Particularly expedient are such forms as Raschig ring bodies, which facilitate the transportation of biogas out of the reactor.

When they are employed, the porous sintered bodies are brought in the dry state into contact with the cell suspension, the micro-organisms being "sucked", together with the fluid, inside the pores, where they can attach to the fine-pore "fissured" walls. In the case of anaerobic processes, the air contained within the pores of the glass bodies must first be conventionally removed by evacuation or displacement by inert gas, in order to avoid poisoning the cells with oxygen. As the reaction continues, the originally virgin surface of the sintered bodies develops a microbial "lawn", which can be clearly recognized by, among other things, a change in color. Unless indicated otherwise herein, all details of the use of the carrier of this invention are conventional, e.g., as disclosed in DE-OS 28 39 580.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Figure 3:
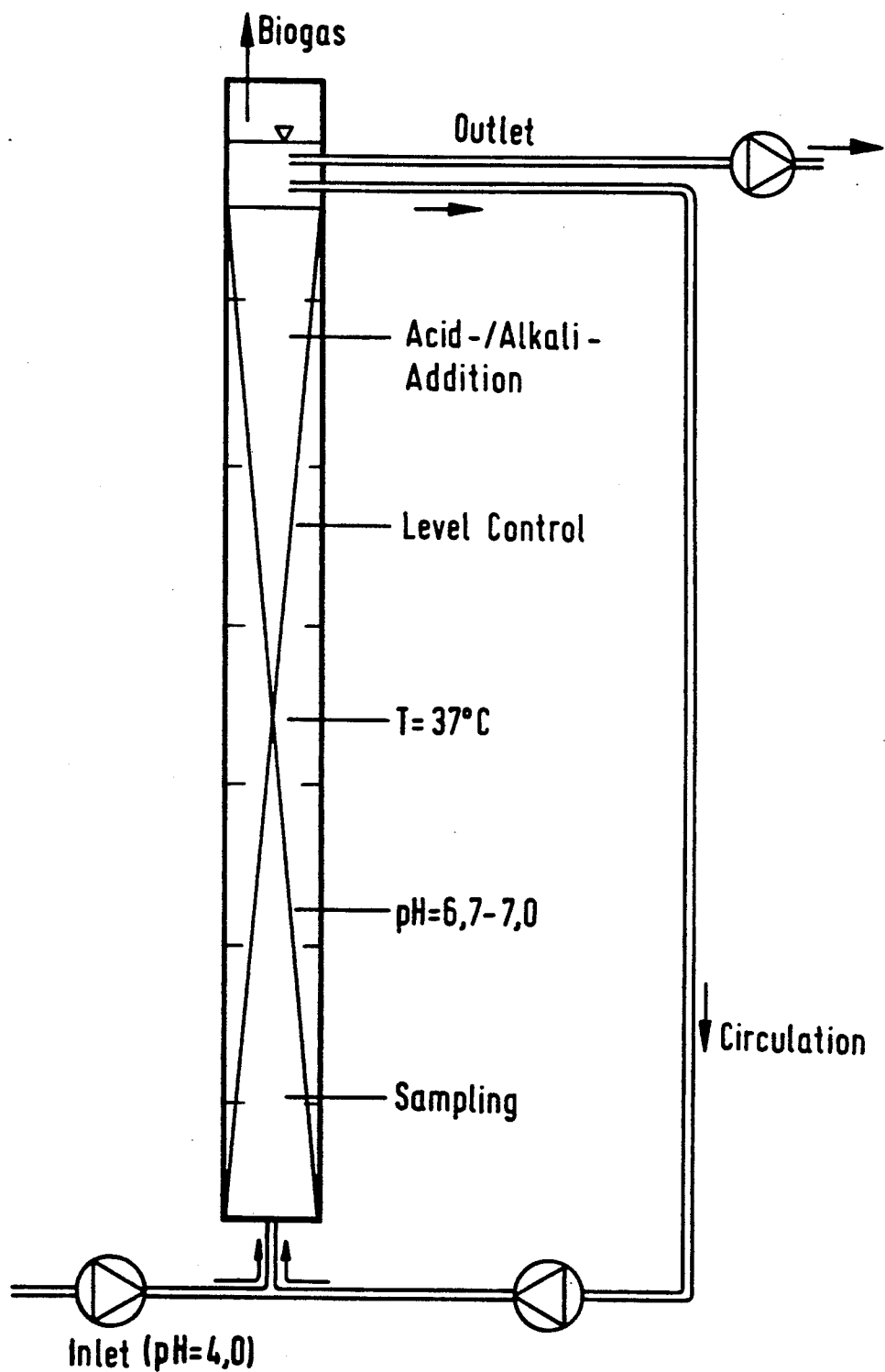
FIG. 3 shows a schematic representation of a continuous-flow reactor.

Into a fixed-bed continuous-flow reactor, as shown in FIG. 3, having a height of 1.2 m, a diameter of 0.12 m, and a working volume of 12 l, 1.4 l of sintered glass bodies in the form of cubes (length of side: 0.5 cm) were placed. The porosity of these bodies was 60%, and the diameter of the macropores between 60 and 100 $\mu$m. The average diameter of the micropores was 1-2 $\mu$m.

To start up the reaction, the air enclosed within the pores of the glass bodies was removed by passing argon through the charge. Then, a suspension of micro-organisms (700 mg dry substance per liter) adapted to the substances contained in an evaporator condensate produced by the cellulose industry and extremely highly contaminated with pollutants, was admitted to the reactor in an amount sufficient to fill the latter. Thereafter, the waste water was allowed to flow in. The pH values were monitored at the top and bottom of the reactor, and the recycling portion automatically checked to ensure a maximum difference in pH of 0.3 pH units, as described in the DE patent application P 33 45 691.7.

Figure 4:
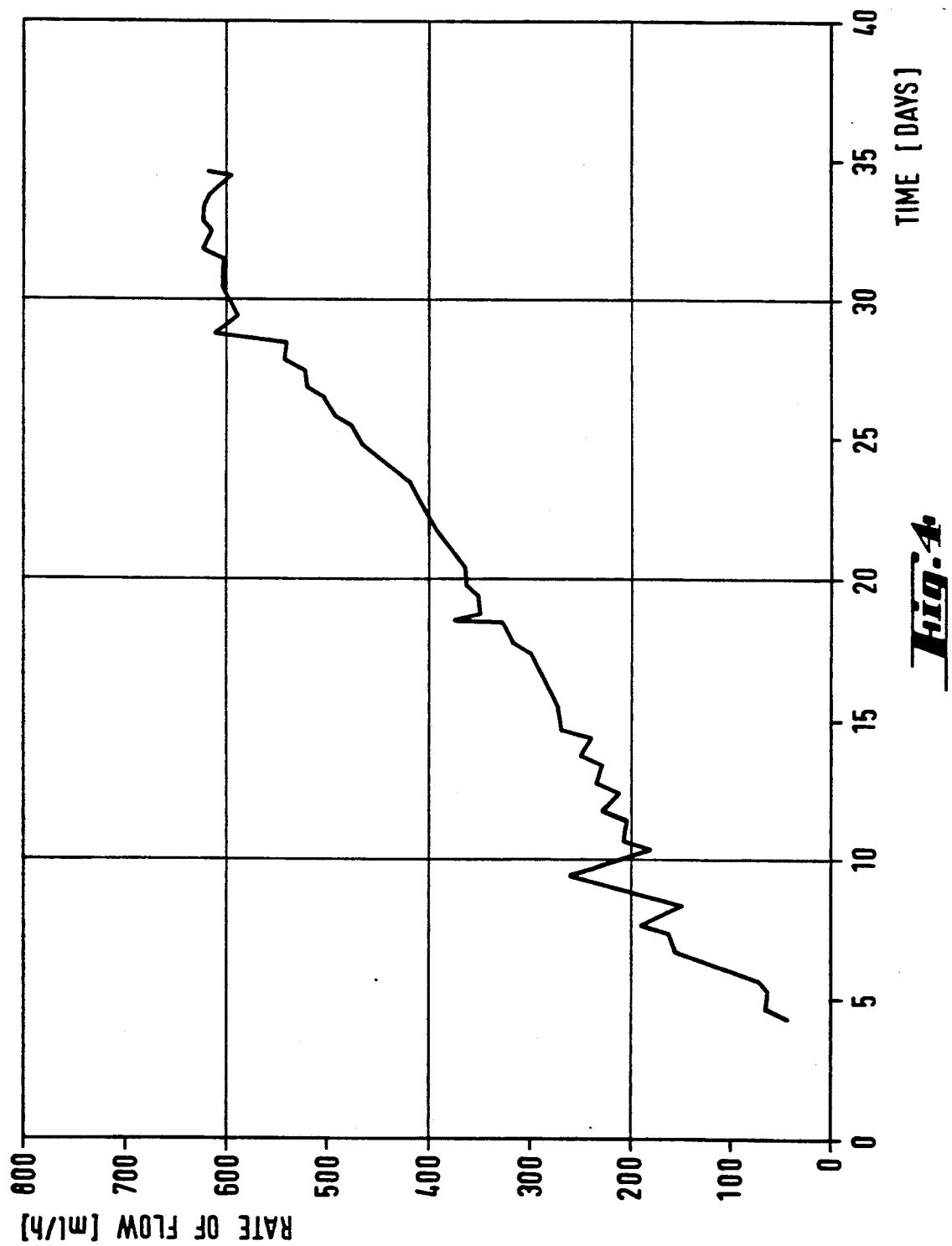
FIG. 4 shows a diagram of waste water throughput as a function of operating time.
Figure 5:
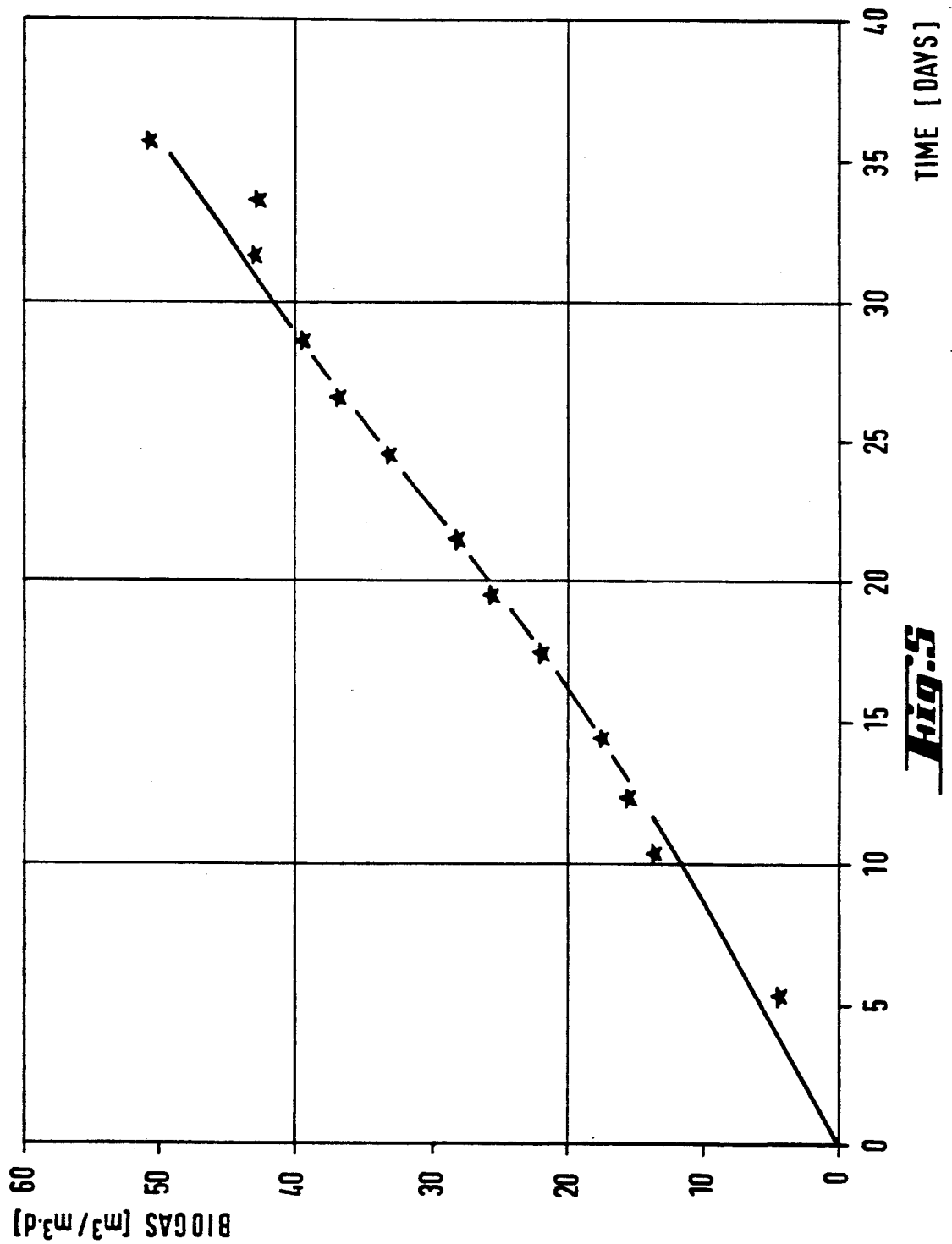
FIG. 5 shows a diagram of biogas production as a function of operating time.

This mode of operation permits the admittance of an amount of waste water that can be "processed" by the micro-organisms, and has the advantage of permitting the starting-up phase to be carried out "gently" (without any danger of over-acidification), while, at the same time, permitting adequate "stressing" of the micro-organisms. Initially, a dwell time of 180 h is employed. Subsequently, however, iterative shortening of the dwell time of the waste water within the reactor is effected by the pH regulator. FIG. 4 shows the linear increase in waste water throughout on starting up the reactor as a function of operating time. In FIG. 5, associated production of biogas is plotted as a function of time. A linear increase in biogas formation (a doubling in about 5.5 days is observed), which, at a dwell time of 12 hours, achieves a value of 51 m$^3$/m$^3$ reactor volume and day. Here, at a space load of 88 kg-CSB/(m$^3$.d), 74 kg-CSB/(m$^3$.d) were eliminated. The results of this trial are summarized in Table 1.

The cubes are produced by sintering a mixture of 50 weight percent NaCl with a grain size of 60 to 120 $\mu$m and 50 weight percent soda-lime-glass (window glass) with a grain size of <20 $\mu$m. The sinter temperature is 730° C. and the sinter time 1 h. After cooling the NaCl is dissolved by water.

TABLE 1

Anaerobic degradation of an evaporator condensate in the fixed-bed continuous-flow reactor with sintered glass as a carrier material (cube form, a = 0.5 cm)

| | |
|---|---|
| Reactor volume: | 12 l |
| Carrier charge: | 7.4 l |
| CSB$_{in}$ (freight inflow): | 44.0 kg/m$^3$ |
| CSB$_{out}$ (freight outflow): | 7.0 kg/m$^3$ |
| Dwell time: | 12 hours |
| Biomass concentration: | 12.44 G/l (from nitrogen analysis) |
| CSB turnover: | 84% |
| Space load: | 88.0 kg-CSB/(m$^3$.d) |
| Sludge load: | 7.0 kg-CSB/(kg.d) |
| CSB elimination: | 74.0 kg(m$^3$.d) |
| Sludge activity: | 5.9 kg-CSB/(kg.d) |
| Biogas formation: | 51.0 m$^3$/(m$^3$.d) |

EXAMPLE 2

In this case, approximately 8 l of a porous sintered glass carrier having the form of Raschig rings (wall thickness: 2 mm, height: 7 mm) having macropores of 60-100 $\mu$m and micropores of 1-2 $\mu$m in diameter, were placed in a reactor of the same size as that in Example 1. The reactor was prepared in the manner described, and filled with a comparable suspension of micro-organisms for the processing of an evaporator condensate as in Example 1. It was found that the increase in waste water throughout and the formation of biogas under conditions otherwise identical with those pertaining in Example 1, occurred more slowly. This correlates with the smaller packing density of Raschig rings in comparison with the cube-shaped carrier bodies. However, after about 6 weeks of operation, a comparably high space-time yield was achieved with the Raschig ring bodies, too. All in all, the use of carrier materials taking the form of Raschig rings proved more favorable than the use of cube-shaped carrier bodies, since the ring charge is more convenient for the flow through the fixed bed and the discharge of gas.

EXAMPLE 3

In a further trial, 7 l of glass carrier material in the form of Raschig rings as in Example 2, were placed in the experimental apparatus as described above. In this case, waste water from a brewery, resulting from the washing of barrels ("barrel water"), was to be treated. This waste water contains mainly sugar, acetic acid and ethanol. The bacterial inoculum was a mixed bacterial culture previously adapted to these contaminants. "Barrel water" is a relatively "lean" waste water, with a chemical oxygen requirement of 2.5-3.5 kg/m$^3$. The reactor was started up in the manner described above (aided by the pH regulator), and the process of iterative dwell time shortening followed-up on the basis of acetic acid and CSB determinations. After 5 weeks of operation, a dwell time of 7 hours was achieved, the chemical oxygen requirement simultaneously being reduced by 94%. The following table summarizes the major degradation data for this trial.

TABLE

| Anaerobic degradation of "barrel water" | |
|---|---|
| Dwell time (t): | 7.6 h |
| $CSB_o$ (inflow): | 2.74 kg/m$^3$ |
| $CSB_e$ (outflow): | 0.21 kg/m$^3$ |
| Space load: | 10.53 kg CSB/(m$^3$.d) |
| CSB turnover: | 93.5% |
| Δ CSB: | 9.85 kg/(m$^3$.d) |
| Biogas formation: | 7.0 m$^3$/(m$^3$.d) |

The relatively short dwell time of 7.6 hours in the reactor in effect means a high space-time yield, and this at an excellent CSB turnover of 93.5%. For the anaerobic degradation of "lean" water, this result is excellent and demonstrates the favorable effect of the biomass immobilized on the porous sintered glass body.

The preceding examples can be repeated with similar success by substituting the generically or specifically described reactants and/or operating conditions of this invention for those used in the preceding examples From the foregoing description, one skilled in the art can easily ascertain the essential characteristics of this invention, and without departing from the spirit and scope thereof, can make various changes and modifications of the invention to adapt it to various usages and conditions The Raschig rings are produced by mixing, extruding and sintering the following mixture in weight percent: 35% $K_2SO_4$ with a grain size of 60 to 120 μm; 35% borosilicate glass ("DURAN") and 30% of a solution of methylcellulose. The sinter temperature is 900° C. and the sinter time 1 h. After cooling to room temperature the $K_2SO_4$ is dissolved in water.

What is claimed is:

1. In a carrier body carrying immobilized microorganisms or animal cells, the improvement wherein the carrier body is a porous carrier body having a double-pore structure of macropores, defined by macropore walls, and micropores positioned in said macropore walls, said macropores permitting a free exchange of liquid and gas throughout the inside of the carrier to the external surroundings, said micropores having a size which is about that of the microorganisms or cells loaded on the carrier, and said carrier body having an open pore volume of 20-80% macropores with a diameter of 20-500 μm and 5-15% micropores with a diameter of 1-10 μm, said carrier having a total open pore volume of 35-85%.

2. In a process of treating a fluid with microorganisms or animal cells comprising contacting the fluid with the microorganisms or cells immobilized on a carrier, the improvement wherein the carrier is a porous carrier body having a double-pore structure of macropores, defined by macropore walls, and micropores positioned in said macropore walls; said carrier body having an open pore volume of 20-80% macropores with a diameter of 20-500 μm and 5-15% micropores with a diameter of 1-10 μm, said carrier having a total open pore volume of 35-85%; said macropores permitting a free exchange of liquid and gas throughout the inside of the carrier to the external surroundings, and said micropores having a size which is about that of the microorganisms or cells loaded on the carrier.

3. In a process of treating a fluid with microorganisms or animal cells comprising contacting the fluid with the microorganisms or cells immobilized on a carrier, the improvement wherein said carrier is prepared by a process comprising sintering a powder mixture of fine-grain sinterable silicated material and a coarse-grain nonsinterable substance melting at a temperature higher than the sintering temperature and separable from the sintered product by dissolution in a compatible solvent, and separating the nonsinterable substance from the sintered product by dissolving it in a compatible solvent, said nonsinterable substance being a salt;

said carrier having an open pore volume of 20-80% macropores with a diameter of 20-500 μm and 5-15% micropores with a diameter of 1-10 μm, said carrier having a total open pore volume of 35-85%;

said macropores of size 20 to 500 μm being obtained by the use in the sintering step of a salt having a grain size of 20-500 μm; and said micropores of size 1-10 μm being obtained by the use in the sintering step of a glass, glass-ceramic or ceramic powder having a grain size <40 μm as said fine-grain sinterable silicated material.

4. A process of claim 3, wherein said fluid is a waste water containing starch and said fluid is treated for the degradation of starch.

5. A process of claim 4, wherein said waste water is brewery waste water.

6. A process of claim 3, carried out in a fixed-bed continuous-flow reactor.

7. A process of claim 3, carried out in a fluidized-bed reactor.

8. A process of claim 3, carried out anaerobically.

9. A process of claim 3, wherein the fluid is treated for purification and is waste water of the paper or cellulose industry.

10. A process of claim 3, which comprises the production of a compound.

11. A process of claim 3, which comprises the production of nutrition-essential or pharmacological substances.

12. A method of immobilizing microorganisms or animal cells on a porous sintered carrier body comprising contacting a sintered carrier body with microorganisms or cells, said carrier body having a double-pore structure with throughgoing macropores permitting a free exchange of liquid and gas from the interior of said carrier body to the external surroundings, and, within the walls of said macropores, open micropores having a diameter about that of the size of said microorganisms or cells, said micropores within the walls of said macropores forming a support region of said carrier body in which said microorganisms or cells are immobilized, and said carrier body having an open pore volume of 20-80% macropores with a diameter of 20-500 μm and 5-15% micropores with a diameter of 1-10 μm, said carrier having a total open pore volume of 35-85%.

13. The method of claim 12, wherein the total open pore volume of the carrier body is 50-70%.

14. The method of claim 12, wherein the total open pore volume of the carrier body is 55-65%.

15. The method of claim 12, wherein the total open pore volume of the carrier body is 50-70% and the percentage of micropores is 5-10%.

16. The method of claim 12, wherein the diameter of the macropores is 20-250 μm.

17. The method of claim 12, wherein the diameter of the macropores is 50-150 μm.

18. The method of claim 12, wherein the carrier body is in the form of a Raschig ring.

19. A method of claim 12, wherein the material of the carrier body contains biologically important trace elements.

20. A method of claim 12, wherein the carrier body has high permeability to fluid through its macropores and has high compatibility with cell growth in its micropores.

21. A method of claim 12, wherein the carrier body is prepared by a process comprising sintering a powder mixture of fine-grain sinterable material having a grain size <40 μm and a coarse-grain nonsinterable substance melting at a temperature higher than the sintering temperature and separable from the sintered product by dissolution in a compatible solvent, and separating the nonsinterable substance from the sintered product by dissolving it in a solvent.

22. A method of claim 21, wherein said fine-grain sinterable material has a grain size <20 μm and a grain-size distribution of about 1 to 5 μm to achieve micropores of about 1 μm.

23. A method of claim 21, wherein said fine-grain sinterable material has a grain size <40 μm and a grain-size distribution of about 5 to 20 μm to achieve micropores of about 10 μm.

24. A method of claim 21, wherein the sinter temperature is 900° C. and the sinter time is 1 hour.

25. A method of claim 21, wherein said fine-grain sinterable material is mixed with a methylcellulose solution.

26. A method of claim 21, wherein said fine-grain sinterable material is a silicated material.

27. A method of claim 21, wherein said fine-grain sinterable material is glass, ceramics or glass-ceramics.

28. A method of claim 27, wherein said fine-grain sinterable material is soda-lime glass, boro-silicate glass, alumino-silicate glass, eucuystite glass-ceramics, cosdiente glass-ceramics or mixtures of 5 to 30% glass and 95 to 70% ceramic-materials.

29. A method of claim 12, further comprising treating a fluid with said microorganisms or animal cells immobilized on said carrier.

30. A method of claim 29, wherein the treatment is carried out in a fixed-bed continuous-flow reactor.

31. A method of claim 29, wherein the treatment is carried out in a fluidized-bed reactor.

32. A method of claim 29, wherein the treatment is carried out anaerobically.

33. A method of claim 29, wherein the fluid is waste water derived from the paper or cellulose industry.

* * * * *